(12) United States Patent
Friedman

(10) Patent No.: US 9,186,324 B2
(45) Date of Patent: Nov. 17, 2015

(54) HAIR FOLLICLE TARGETING COMPOSITIONS

(75) Inventor: Doron Friedman, Karme-Yosef (IL)

(73) Assignee: J.P.M.E.D. LTD., Karme-y Osef (IL)

( * ) Notice: Subject to any disclaimer, the term of this patent is extended or adjusted under 35 U.S.C. 154(b) by 0 days.

(21) Appl. No.: 13/576,407

(22) PCT Filed: Feb. 2, 2011

(86) PCT No.: PCT/IL2011/000122
§ 371 (c)(1),
(2), (4) Date: Aug. 1, 2012

(87) PCT Pub. No.: WO2011/095970
PCT Pub. Date: Aug. 11, 2011

(65) Prior Publication Data
US 2012/0301527 A1 Nov. 29, 2012

(30) Foreign Application Priority Data
Feb. 7, 2010 (IL) .......................................... 203770

(51) Int. Cl.
| | | |
|---|---|---|
| *A61K 8/06* | (2006.01) | |
| *A61K 9/107* | (2006.01) | |
| *A61K 8/92* | (2006.01) | |
| *A61K 9/00* | (2006.01) | |
| *A61K 31/00* | (2006.01) | |
| *A61Q 9/00* | (2006.01) | |
| *A61K 47/10* | (2006.01) | |
| *A61K 47/14* | (2006.01) | |
| *A61Q 5/00* | (2006.01) | |

(52) U.S. Cl.
CPC . *A61K 9/107* (2013.01); *A61K 8/06* (2013.01); *A61K 8/92* (2013.01); *A61K 9/0014* (2013.01); *A61K 31/00* (2013.01); *A61K 47/10* (2013.01); *A61K 47/14* (2013.01); *A61Q 9/00* (2013.01); *A61K 2800/81* (2013.01); *A61Q 5/00* (2013.01)

(58) Field of Classification Search
CPC ........... A61K 8/06; A61K 8/92; A61K 9/107; A61K 47/14
USPC ........................... 424/401, 70.1; 514/171, 1.1
See application file for complete search history.

(56) References Cited

U.S. PATENT DOCUMENTS

| | | | | |
|---|---|---|---|---|
| 5,034,221 | A * | 7/1991 | Rosen et al. .................... 424/73 |
| 6,342,238 | B1 * | 1/2002 | Simonnet et al. ............. 424/401 |
| 7,393,548 | B2 * | 7/2008 | Friedman ...................... 424/725 |
| 2003/0108611 | A1 * | 6/2003 | Bosch et al. .................. 424/489 |
| 2005/0226900 | A1 | 10/2005 | Winton Brooks et al. |
| 2007/0239144 | A1 | 10/2007 | Korenberg |
| 2008/0138296 | A1 * | 6/2008 | Tamarkin et al. ............... 424/47 |
| 2009/0149796 | A1 * | 6/2009 | Jones et al. .................... 604/20 |

OTHER PUBLICATIONS

Vitamine A; University of Maryland Medical center, downloaded from http://umm.edu/health/medical/altmed/supplement/vitamina-retinol; Jan. 3, 2015.*
Wang et al.; Title: Susceptibility of Propionibacterium acnes to Seventeen Antibiotics; Antimicrob Agents Chemother.; 11(1): 171-173; Jan. 1977.*

* cited by examiner

*Primary Examiner* — Johann R Ricter
*Assistant Examiner* — Yanzhi Zhang
(74) *Attorney, Agent, or Firm* — Neifeld IP Law, PC

(57) ABSTRACT

This invention provides topical pharmaceutical or cosmetic compositions, and uses thereof in treating a disease or condition of the hair follicle. The compositions of this invention are emulsions of an oil-in-polyol with a mean particle size of below one micron, and further comprising at least one oil, one polyol, and one stabilizer.

12 Claims, 1 Drawing Sheet

HAIR FOLLICLE TARGETING COMPOSITIONS

This application is a U.S. national stage entry of PCT/IL2011/000122, filed 2 Feb. 2011.

BACKGROUND OF THE INVENTION

Hair grows on human skin in various textures, colors, and density. The structure from which each hair grows is called a follicle. Muscles, oil glands (sebaceous glands), and nerves extend from the follicle into the next layer of the skin—the dermis. Throughout life, the skin is constantly shedding dead skin cells and growing new ones. This happens all over the skin. Inside the follicles, sebum (oil) carries the dead cells to the surface. Various factors can interfere with the cycle of renewal and disposal, and a number of disorders can result.

Skin Follicle diseases include infectious diseases, immunological disorders, blockage of sebaceous gland or of all hair follicle, cancers, and multiple cause inflammatory conditions.

Folliculitis is the infection and inflammation of the hair follicles. The condition may be superficial (i.e., on the surface of the skin) or deep within the follicles. Hair follicles become red and irritated, and pus-filled lesions form. Folliculitis can clear up by itself in a matter of a couple of weeks or become more persistent and thus require treatment. The most common cause of folliculitis is infection by the bacteria *Staphylococcus aureus*. Other species of bacteria may also be responsible. For example, contaminated water in whirlpools and hot tubs can transmit *Pseudomonas aeruginosa*, which can cause folliculitis. This bacterium may also be passed in wet suits. Fungal and viral infections can also cause the condition. These are not common, but doctors may suspect these agents if conventional treatments do not work. Viral infections may be more common in those with compromised immune systems, such as AIDS, organ transplant, and cancer patients.

Folliculitis symptoms can appear independent of infection. Exposure of the skin to certain chemicals, especially oils and tars, can trigger an outbreak. People with depressed immune systems, diabetes, or obesity have a greater risk of contracting folliculitis than the general population. An early sign of folliculitis is a small white or yellow pus-filled lesion (pustule) on a red, inflamed follicle. The most likely starting points are the scalp, thighs, legs, and buttocks. When an infection of the follicle goes deeper, it becomes a boil or furuncle. A group of closely packed boils create a larger lesion called a carbuncle. These lesions tend to occur in hairy, sweaty areas of the body.

*Hidradenitis suppurativa* is a potentially serious, chronic, pus-producing (suppurative) disorder of the follicles and sweat glands. *Hidradenitis suppurativa* develops primarily in the sweat glands located in the armpits, in the groin, around the breasts, and in the anal region. The follicles and ducts become blocked, and bacteria and pus are forced into the surrounding tissue, causing irritation. Abscesses form and can become quite large and eventually break through the skin. Abscesses may open and drain spontaneously. Scar tissue forms in the healing process. *Hidradenitis suppurativa* can be a socially and physically painful and disabling disease. The bacterium *Staphylococcus aureus* is usually involved in the condition, and *Proteus* species are often involved in chronic cases. Bacteria called coagulase-negative staphylococci (CNS) have also been associated with these infections.

There seems to be a genetic predisposition for the disease, and it seems to be more common in women. *Hidradenitis suppurative* does not appear in people who have not reached puberty because the sweat glands are not active, but it can appear at any age afterward. *Hidradenitis suppurativa* affects people who are extremely overweight (obese) at a higher rate than the general population. Cigarette smokers also have a higher incidence of this disorder than nonsmokers.

Signs of *hidradenitis* are firm red nodules that are usually located under the arm, in the groin, around the breasts, or around the anus. Pustules and abscesses may discharge pus spontaneously and heal slowly, resulting in scar tissue. The appearance of nodules recurs periodically throughout the year. Heat, perspiration, and being overweight can aggravate the condition. Pain is a common symptom in chronic disease. Over time, fibers of scar tissue branch out, creating restrictive, tight skin. This can interfere with movement of the arms or legs, if the sweat glands in the armpits or groin are involved. Dermatologists diagnose the disorder by the appearance and location of the lesions. Infection and inflammation can spread beyond the sweat glands into cells located in the deep layers of the skin and in muscle tissue. This condition is called cellulitis. The skin covering the infected area is usually warm and tender.

*Keratosis pilaris* is a condition in which the hair follicles become blocked with hair and dead cells from the outermost layer of skin (epidermis). The follicles redden and inflame causing bumps (papules) to develop. The papules of *keratosis pilaris* usually occur on the upper arms and thighs, but also appear on the face, back, and buttocks.

*Keratosis pilaris* (KP) is a hereditary disorder. One can inherit it from one or both parents. KP stems from overreproduction of keratinocytes, the cells that manufacture the protein keratin, an important skin component (called hyperkeratosis). Some researchers describe KP as one of a whole spectrum of disorders, rather than as an independent disease. KP is more prevalent among children and adolescents and less common in adults. It seems to improve after puberty. Individuals with dry skin and eczema (skin disorder) tend to have more severe cases. The condition improves during warm summer months and worsens during the winter. The signs of *keratosis pilaris* are the papules that typically appear on the upper arms and thighs, and sometimes on the back, face, and buttocks. Papules re-form after they have been removed.

Perioral dermatitis (POD) is a disorder of the follicles in which pink bumps (papules) appear around the mouth and sometimes around the eyes. POD is most common in 20- to 50-year-old women, but occurs in men and children as well. The causes of POD are not well understood. There is some evidence that fungi and bacteria may be underlying causes of the disorder. However, this has not been proven.

People who use topical corticosteroids (anti-inflammatory drugs) for other skin disorders on the face have a higher rate of POD than the general population. Stress also plays a role, as does repeatedly touching the skin on the face. Dermatologists usually diagnose POD by the occurrence of pink papules around the mouth. Often the papules develop around the eyes and nostrils as well. The next stage of POD brings scaling and reddening. Some patients experience burning and itching. POD has a tendency to improve and worsen at variable intervals.

Rosacea is a disorder of the follicles and surrounding skin that usually occurs on the forehead, nose, and chin. It involves reddening, acnelike lesions, and broken blood vessels. Rosacea improves and worsens in unpredictable cycles. The exact cause is unknown. Although rosacea can appear at any age, it is most prevalent between 30 and 60 years old. It occurs about equally in men and women, although severe cases are more common in men. Rosacea seems to have a genetic component. Individuals whose family members have rosacea have a higher incidence of the disorder. Emotional and physical stress, windy conditions, heat, and sun exposure can exacerbate rosacea. Dietary triggers include dairy products, certain spices, hot liquids, and alcohol.

Some people with stomach ulcers are prone to develop rosacea. The cause of a high percentage of stomach ulcers is infection with the bacterium *Heliobacter pylori* (*H. pylori*). While studies are still inconclusive, eradication of *H. pylori* in ulcer patients can lead to improvement in rosacea. There is increasing evidence that this bacterium causes a variety of systemic disorders. However, rosacea appears without *H. pylori* and vice versa.

Doctors usually diagnose rosacea by observing the appearance of the skin. Not all redness, flushing, and blushing is caused by rosacea. However, redness that takes a long time to clear up, or never clears up, often indicates rosacea. Acne pustules sometimes develop with this condition; however, blackheads are not a hallmark. Bacterial infections can contribute to inflammation. As the disorder progresses, the patient's facial skin exhibits broken blood vessels. A rare symptom is rhinophyma, a thick, leathery texture of the nose skin. The eyes can be affected with irritation and increased light sensitivity.

Acne is also a hair follicle disease whereas follicles are finally clogged and become infected and inflamed. Acne is an inflammatory skin disorder of the skin's sebaceous glands and hair follicles that affects about 80% of people between the ages of 12 and 24. There is a genetic propensity for follicular epidermal hyperproliferation with subsequent plugging of the follicle. Retention hyperkeratosis is the first recognized event in the development of acne vulgaris. Excess sebum is another key factor in the development of acne vulgaris. Sebum production and excretion are regulated by a number of different hormones and mediators. P acnes is an anaerobic organism present in acne lesions. The presence of P acnes promotes inflammation through a variety of mechanisms. P acnes stimulates inflammation by producing proinflammatory mediators that diffuse through the follicle wall.

Alopecia is a condition affecting humans, in which hair is lost from some or all areas of the body, usually from the scalp. Alopecia may occure as consequence of genetics or following chemotherapy and radiation. Treating or preventing of common Alopecia and treating chemotherapy induced alopecia may be achieved with hair growth stimulators that are generally well known, and include minoxidil, substance-P, cyclosporin, cyclosporin A, finesteride, and the like known hair growth stimulators.

The primary principle behind laser hair removal is selective photothermolysis (SPTL) Lasers can cause localized damage by selectively heating dark target matter, (melanin), in the area that causes hair growth, (the follicle), while not heating the rest of the skin. Light is absorbed by dark objects, so laser energy can be absorbed by dark material in the skin (but with much more speed and intensity). This dark target matter, or chromophore, can be naturally-occurring or artificially introduced.

Hair removal lasers selectively target melanin: Melanin is considered the primary chromophore for all hair removal lasers currently on the market. Melanin occurs naturally in the skin (it gives skin and hair its color). There are two types of melanin in hair: eumelanin (which gives hair brown or black color) and pheomelanin (which gives hair blonde or red color). Because of the selective absorption of photons of laser light, only black or brown hair can be removed.

Both men and women seek laser hair removal services to have superfluous or unwanted hair removed. Hair removal is commonly done on lip, chin, ear lobe, shoulders, back, underarm, abdomen, buttocks, pubic area, bikini lines, thighs, face, neck, cleavage, chest, arms, legs, hands, and toes. Laser works best with dark coarse hair. Light skin and dark hair are an ideal combination, but new lasers are now able to target dark black hair even in patients with dark skin However, Laser hair removal of blond and white hair is a complicated task with often unsatisfactory results as a result of a lack of laser-absorbing chromophore. Attempts to introduce Liposome encapsulated melanin (Lipoxome; Dalton Medicare B.V., Zevenbergschen Hoek, The Netherlands) into the hair follicles were not successful. (Ann Plast Surg. 2007 May; 58(5):551-4. (A randomized, controlled, double-blind study evaluating melanin-encapsulated liposomes as a chromophore for laser hair removal of blond, white, and gray hair. Sand M, Bechara F G, Sand D, Altmeyer P, Hoffmann K.)

White gray or blond hair does not respond effectively to Laser selective photothermolysis treatment and thus pose an unmet need. Practically, people suffering from unwanted non-pigmented hair grow (white, gray or light blond) could not be effectively treated with photothermolysis. Attempts to artificially introduce melanin into the hair follicle by Liposome melanin require many applications each day over few days whereas pigmenting the hair follicles with current application by various pigments occurs within one day and one to three single applications.

Lingna and Valeryi U.S. Pat. Nos. 5,914,126 and 5,753,263 disclose liposomes that target preferentially hair follicle. However liposomes are difficult to produce and to stabilize and have limited loading capacity and very low unfavorable loading yield, making them inferior for industrial production.

There is therefore a need for a vehicle or carrier which is a delivery system that will effectively deliver drugs or cosmetic agents to the hair follicle cavity, that will be simple to produce and develop, have high load and yield and provide effective hair follicle targeting and accumulation.

SUMMARY OF THE INVENTION

In one embodiment, this invention provides a topical pharmaceutical or cosmetic composition, which is an emulsion of an oil-in-polyol with a mean particle size of below one micron, and further comprising at least one oil, one polyol, and one stabilizer, for the specific targeting and for accumulation within a hair follicle.

In one embodiment, this invention further provides for the use of a topical pharmaceutical or cosmetic composition of this invention, in the preparation of a medicament for use in treating a disease or condition of the hair follicle.

In another embodiment, this invention further provides for a method of cosmetic treatment or beautification of hair in a subject, said method comprising administering a topical cosmetic composition of this invention to the hair of said subject.

In another embodiment, this invention further provides for a method of hair removal in a subject, said method comprising administering a topical cosmetic composition of this invention to said subject, wherein said composition further comprises an agent, which is a depilatory.

In another embodiment, the invention provides a method of hair removal in a subject, the method comprising administering a topical cosmetic composition of this invention to said subject further comprising a coloring agent, and applying laser photothermolysis for hair removal in said subject, wherein said coloring agent facilitates the laser photothermolysis.

BRIEF DESCRIPTION OF THE DRAWINGS

Various embodiments of compositions and applications thereof are described herein with reference to the figures wherein:

FIG. 3 shows a histogram of an oil-in-glycerin emulsion composition particle size by DLS.

DETAILED DESCRIPTION OF THE INVENTION

Figure 1:
FIG. 1 the arrow depicts the targeting of Fluorescein Dilaurate oil-in-glycerin emulsion composition to hair follicles.

This invention provides, in some embodiments, for a topical pharmaceutical or cosmetic composition, which is an emulsion of an oil-in-polyol with a mean particle size of below one micron, and further comprising at least one oil, one polyol, and one stabilizer, for the specific targeting and for accumulation within a hair follicle.

The invention also provides for any device, bandage, patch, or other implement which incorporates such composition there-within.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The compositions of the invention comprise an oil-in-polyol emulsion, which in turn comprises at least one oil, one polyol, and at least one stabilizing agent. Applicants have surprisingly found that such compositions, when the mean particle is below 1 micron, or a majority of the particles in such composition, or at least 50% of the particles of such composition are of a size of less than 1 micron, i.e. on a nanometer scale, result in specific accumulation within hair follicles.

Exemplified herein is a model system, whereby a marker molecule, Fluorescein Dilauratre (FD) incorporated in Vaseline or in, emulsions of mean droplet size of two to ten micron and no sub-micron particles showed minimal to no hair follicle targeting in comparison to excellent hair follicle targeting and accumulation of a composition containing FD formulated in an oil-in-polyol vehicle having a mean particle size which was sub-micron, (below 1,000 nanometers).

An oil-in-polyol emulsion composition internal phase is the oil phase having an average particle or droplet size of below two microns, or in some embodiments, below one micron, or in some embodiments, 200 to 1,000 nanometers or in some embodiments, 300 to 800 nanometers.

The polydispersity of the mean droplet size is not critical in terms of generating a composition of this invention with the noted advantage of targeting the hair follicle. In some embodiments, however, at least 50% of droplets on number average in the composition are of a size of below one micron. In some embodiments, at least 90% of the oil droplets have a size of 200-2,000 nanometers, or in some embodiments, at least 90% of the oil droplets have a size of 200-1,000 nanometers.

The compositions of this invention will comprise at least one stabilizer, which in one embodiment is an emulsifier.

The compositions of this invention may comprise a penetration enhancer.

In some embodiments, the oil component of the compositions of this invention will be any appropriate oil known to the skilled artisan. Non-limiting examples may include any vegetable or animal or synthetic or mineral or silicon oil, such as vegetable triglyceride, avocado oil, coconut oil, isopropyl myristate, mineral oil, squalene, petroleum gelly, lanoline, and their esters or derivatives, and combinations or blends thereof, and others.

In some embodiments, the polyol component of the compositions of this invention will be any appropriate polyol known to the skilled artisan. Non-limiting examples may include glycerin, propylene glycol, hexylene glycol, butylenes glycol, glycofurol, polyethylene glycols (PEG) such as PEG400, PEG 1500, PEGs 4000 or PEG 6000, and others, as will be appreciated by the skilled artisan.

The skilled artisan will appreciate how the compositions of this invention are prepared. For example, and in one embodiment, the component of two phases, the oil phase and the polyol phase can be heated separately to about 70° Celsius until the waxes and stabilizing agents are fully solubilized, and the composition is homogenized and cooled to room temperature. Any additive can be added to the oily phase or polyol phase in the production process while heating or homogenizing or mixed with the ready emulsion, as will be understood by the skilled in the art. The oil-in-polyol emulsion is produced, in some embodiments, under vigorous homogenization, high shear homogenization, pressure or microfluidizer, piston or extrusion homogenization.

The particle size can be readily assessed, as will be appreciated by the skilled artisan. For example, size characterization may be by microscopy, differential light scattering (DLS) and others, as will be appreciated by the skilled artisan. Hair follicle targeting and accumulation can be similarly assessed. For Example, FIGS. 1-3 demonstrate detection of accumulation of the composition within a hair follicle and characterization of the particle size, respectively.

The compositions of this invention may further comprise at least one therapeutic agent.

In some embodiments, the term "therapeutic agent" will be understood to encompass any agent, which provides a therapeutically desirable effect when administered to an animal (e.g. a mammal, such as a human) in effective amounts, it being understood that not all subjects will benefit from the agent.

In some embodiments, the therapeutic agent is a drug. In some embodiments, the therapeutic agent is an antibiotic, antiviral or antifungal agent.

In some embodiments, the composition may further comprise an adjuvant, an antigen, an immuno-stimulatory compound, a chemotherapeutic or a combination thereof.

In one or more embodiments, the therapeutic agent may comprise active herbal extracts, acaricides, age spot and keratose removing agents, allergen, analgesics, local anesthetics, antiacne agents, antiallergic agents, antiaging agents, antibacterials, antibiotics, antibum agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, anti-yeast agents, astringents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non steroidal anti-inflammatory agents, oxidizing agents, pediculicides, photodynamic therapy agents, retinoids, sanatives, scabicides, self tanning agents, skin whitening agents, vitamins, vitamin D derivatives, wound healing agents and wart removers.

Non-limiting examples of antibiotic drugs include amoxicillin, ampicillin, aztreonam, biapenem, carbenecillin, cefaclor, cefadroxil, cefamandole, cefatrizine, cefoxitin, clavulanic acid, dicloxacillin, imipenem, meclocycline, methacycline, moxalactam, panipenem, sulbactam, azithromycin, erythromycin, josamycin, miokamycin, rifabutine, rifamide, rifamycin, gentamicin, paromomycin, sisomicin, bacampicillin, carbomycin, clindamycin, ciprofloxacin, clinafloxacin, difloxacin, enrofloxacin, lomefloxacin, nadifloxacin, norfloxacin, ofloxacin, pipemidic acid, apicycline, clomocycline, oxytetracycline, nifurpirinol, nifurprazine, isoniazid, rifampin, rifapentine, dapsone, thiazolsulfone, sulfamethoxazole, sulfamoxole, metronidazole.

Non-limiting examples of antiviral drugs include acyclovir, famciclovir, ganciclovir, penciclovir, ribavirin, vidarabine, zidovudine.

Non-limiting examples of antifungal drugs include amphotericin B, glucan synthesis inhibitors such as caspofungin, micafungin, or anidulafungin (LY303366), econazole, terconazole, fluconazole, voriconazole or griseofulvin.

The therapeutic agent may include an anti-tumoral agent. Non-limiting examples of anti-tumoral drugs may include ancitabine, anthramycin, azacitidine, azaserine, 6-azauridine, bicalutamide, carubicin, carzinophilin, chlorambucil, chlorozotocin, cytarabine, daunorubicin, defosfamide, demecolcine, denopterin, 6-diazo-5-oxo-L-norleucine, docetaxel, doxifluridine, doxorubicin, droloxifene, edatrexate, eflornithine, enocitabine, epirubicin, epitiostanol, etanidazole, etoposide, fenretinide, fludarabine, fluorouracil, gemcitabine, hexestrol, idarubicin, lonidamine, mannomustine, melphalan, menogaril, 6-mercaptopurine, methotrexate, mitobronitol, mitolactol, mitomycins, mitoxantrone, mopidamol, mycophenolic acid, ninopterin, nogalamycin, paclitaxel, pentostatin, pirarubicin, piritrexim, plicamycin, podophyllic acid, porfimer sodium, porfiromycin, propagermanium, puromycin, ranimustine, retinoic acid, roquinimex, streptonigrin, streptozocin, teniposide, tenuazonic acid, thiamiprine, thioguanine, tomudex, topotecan, trimetrexate, tubercidin, ubenimex, vinblastine, vincristine, vindesine, vinorelbine or zorubicin.

The therapeutic agent may include an anti-inflammatory agent. Non-limiting examples of anti-inflammatory drugs may include aceclofenac, acemetacin, acetylsalicylic acid, 5-amino-acetylsalicylic acid, alclofenac, alminoprofen, amfenac, bendazac, bermoprofen, .alpha.-bisabolol, bromfenac, bromosaligenin, bucloxic acid, butibufen, carprofen, cinmetacin, clidanac, clopirac, diclofenac sodium, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glucametacin, glycol salicylate, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, naproxen, niflumic acid, oxaceprol, oxaprozin, oxyphenbutazone, parsalmide, perisoxal, phenyl acetylsalicylate, olsalazine, pyrazolac, piroxicam, pirprofen, pranoprofen, protizinic acid, salacetamide, salicilamide O-acetic acid, salicylsulphuric acid, salsalate, sulindac, suprofen, suxibuzone, tenoxicam, tiaprofenic acid, tiaramide, tinoridine, tolfenamic acid, tolmetin, tropesin, xenbucin, ximoprofen, zaltoprofen, zomepirac, tomoxiprol or sulindac.

The therapeutic agent may include an analgesic. Non-limiting examples of analgesics may include acetaminophen (paracetamol), acetaminosalol, aminochlorthenoxazin, acetylsalicylic 2-amino-4-picoline acid, acetylsalicylsalicylic acid, anileridine, benoxaprofen benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypethidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit or paracetamol.

The therapeutic agent may include a steroidal compound. Non-limiting examples of steroidal compounds may include Budesonide, Hydrocortisone, Alclomethasone, Algestone, Beclomethasone, Betamethasone, Chloroprednisone, Clobetasol, Clobetasone, Clocortolone, Cloprednol, Cortisone, Corticosterone, Deflazacort, Desonide, Desoximethasone, Dexamethasone, Diflorasone Diflucortolone, Difluprednate, Fluazacort, Flucloronide, Flumethasone, Flunisolide, Fluocinolone Acetonide, Fluocinonide, Fluocortyn Butyl, Fluocortolone, Fluorometholone, Fluperolone Acetate, Fluprednidene Acetate, Fluprednisolone, Flurandrenolide, Formocortal, Halcinonide, Halobetasol Propionate, Halomethasone, Halopredone Acetate, Hydrocortamate, Loteprednol Etabonate, Medrysone, Meprednisone, Methylprednisolone, Momethasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Triamcinolone, Triamcinolone, Acetonide, 21-Acetoxypregnenolone, Cortivazol, Amcinonide, Fluticasone Propionate, Mazipredone, Tixocortol, Triamcinolone Hexacetonide, Ursodesoxycholic acid, Chenodeoxycholic acid, Mitatrienediol, Moxestrol, Ethynylestradiol, Estradiol or Mestranol.

The therapeutic agent may include a peptide, polypeptides or proteins or nucleotide, for example are an anti-allergic peptides, a Keratinocyte growth factor or an siRNA.

The therapeutic agent may include beta carotenes, astaxanthins, lycopene, anti-oxidants, soy diadezin, genistein, polypehnols, quercetin and derivatives, curcumin, pigments and coloring agents, herbal extracts such as *Saw palmetto* oil, *Rosemarine* extract, *Hypericum* extract and/or *Opuntia* extract.

A cosmetic agent may include a coloring agent such as Sudan Black, Chlorophyll, Phtalocyaniones, Henna, Melanin and the like.

In some embodiments, the compositions of this invention are in the form of a shampoo, a conditioner, a spray, a gel, a mask, a cream, a lotion, an ointment, an oil, a liquid or a mousse.

In some embodiments, the compositions of this invention are formulated to contain a therapeutic agent in an amount of, for example, 0.0001 to 50% w/w, e.g. 0.075 to 20% w/w (including therapeutic agent (s) in a range between 0.1% and 20% in increments of 0.1% w/w such as 0.6% w/w, 0.7% w/w, etc.), often 0.2 to 15% w/w and most often 0.5 to 10% w/w).

In some embodiments, when formulated in an ointment, the active ingredients may be employed with either a paraffinic or a water-miscible ointment base. In some embodiments, the active ingredients may be formulated in a cream with an oil-in-water cream base.

In some embodiments, the composition may include, a polyhydric alcohol, propylene glycol, butane 1,3-diol, mannitol, sorbitol, glycerol and polyethylene glycol (including PEG 400) and mixtures thereof. In some embodiments, the topical formulations may include a compound that enhances absorption or penetration of the active ingredient(s) through the skin or other affected areas. Examples of such dermal penetration enhancers include dimethyl sulphoxide and related analogs.

In some embodiments, the compositions of this invention may make use of emulgents and/or emulsion stabilizers, such as, for example, Tweens, Spans, Brijs, Sucrose esters, Alkyl glucoside, Alkyl polyglycosides, polyglyceryl esters, tocopheryl polyethylene glycol succinate, cetostearyl alcohol, benzyl alcohol, myristyl alcohol, glyceryl mono-stearate and/or sodium lauryl sulfate. Extensive list of optional surfactants is provided for example by Degussa™ GMBH or Cognis™ England.

In some embodiments, the choice of suitable oils or fats for the formulation may also be a reflection of the ability to achieve the desired cosmetic properties. Creams are generally non-greasy, non-staining and washable products with suitable consistency to avoid leakage from tubes or other containers. Straight- or branched-chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. In some embodiments, high melting point lipids such as white soft paraffin and/or liquid paraffin or other mineral oils are used.

In some embodiments, the invention provides for the use of a topical pharmaceutical or cosmetic composition of this invention, in the preparation of a medicament for use in treating a disease or condition of the hair follicle.

In some embodiments, the invention provides a method of treatment of a disease or condition of the follicle, the method comprising contacting a region of the body having hairs with a topical pharmaceutical or cosmetic composition of this invention, where the composition comprises a therapeutic agent, and the contact results in the penetration and accumulation of the therapeutic agent within the hair follicle.

In some embodiments, this invention provides a method of treating, delaying progression of, prolonging remission of, or reducing the incidence or severity of cancer in a subject, via administering to the subject a composition of this invention. According to this aspect, and in some embodiments, the composition may comprise an anti-cancer compound. In some embodiments, such method of treatment may be accompanied by adjunct anti-cancer therapy.

In some embodiments, this invention provides a method of cosmetic treatment or beautification of hair in a subject, said method comprising administering a topical cosmetic composition of this invention to the hair of said subject.

In some embodiments, this invention provides a method of hair removal in a subject, said method comprising administering a topical cosmetic composition of this invention to said subject, wherein said composition further comprises an agent, which is a depilatory.

As indicated above, the present invention may, in some aspects, concern the inhibition of hair growth, and consequent hair removal, and is applicable to a number of different therapeutic, cosmetic, and industrial applications therefore.

It is to be understood that the methods and/or compositions of this invention which by affecting/modulating an immune response, in turn prevent disease, and/or ameliorate disease, and/or alter disease progression are to be considered as part of this invention.

In some embodiments, the term "contacting" or "administering" refers to both direct and indirect exposure to the indicated material.

It is to be understood that repeated use of reference characters in the present specification and drawings is intended to represent the same or analogous features of the invention.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format The following examples describe certain embodiments of the invention and and should not be construed as limiting the scope of what is encompassed by the invention in any way.

EXAMPLES

Example 1

Fluorescein Dilaurate Emulsion

Fluorescein Dilaurate (FD) was incorporated into oil-in-polyol emulsion with mean particle size of below one micron and dissolved in Vaseline. Table 1 below describes the ingredients used in formulating the FD in oil-in-polyol emulsion of

TABLE 1

| Ingredients | 1 Oil-in-polyol % W/W | 2 Vaseline % W/W |
|---|---|---|
| Fluorescein Dilaurate | 1.0 | 1.0 |
| Vaseline | | 99.0 |
| Capric/Caprylic triglycerides | 10.0 | |
| Decyl glucoside/Stearic acid (Montanov 68 ™) | 4.0 | |
| Glycerin | 63.0 | |
| Water | 20.0 | |
| Total | 100 | 100 |

Figure 2:
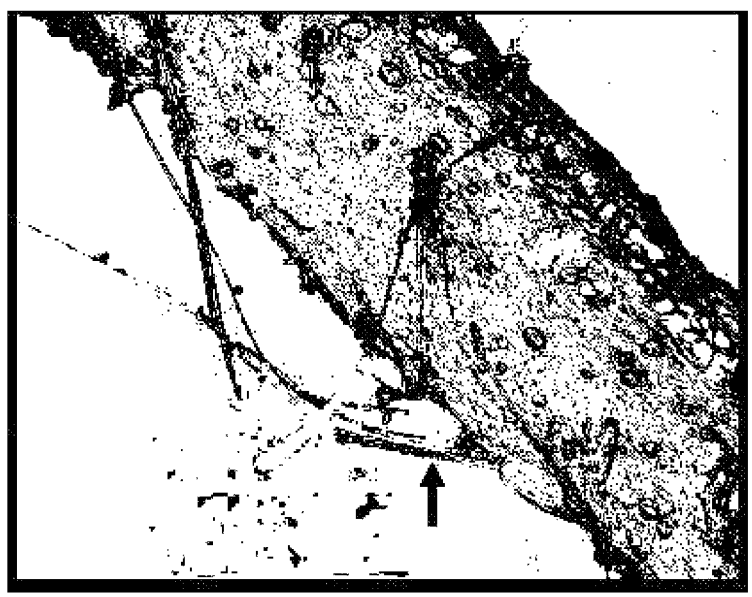
FIG. 2 the arrow depicts the lack of appreciable targeting of Fliorescein Dilaurate dissolved in Vaseline to hair follicles.

Fluorescein Dilaurate in the formulation in table 1 was applied on pre-shaved mice and a skin biopsy was taken at one and three hours after application. Hair follicles of the skin biopsy loaded with the product of FD in oil-in-polyol emulsion, formulation 1 are shown in FIG. 1. Clearance of FD after application of formulation 2, where FD is dissolved in a Vaseline vehicle is shown in FIG. 2. FIG. 3 depicts a differential light scattering (DLS) histogram of the the oil-in-glycerin emulsion composition, indicating the particle size. The particles were dispersed in water.

Example 2

Beta Carotene Emulsion

Five different formulations of a Beta carotene in oil-in-polyol vehicle were produced. Table 2 below lists the ingredients used in each of the formulations (A-E).

TABLE 2

| Ingredients | A % W/W | B % W/W | C % W/W | D % W/W | E % W/W |
|---|---|---|---|---|---|
| Beta carotene | 0.5 | 0.5 | 0.5 | 0.5 | 0.5 |
| Capric/Caprylic triglycerides | 12.0 | — | 12.0 | 6.0 | 6.0 |
| Isopropyl myristate | — | 6.0 | — | 6.0 | 6.0 |
| Octyl dodecanol | — | 6.0 | 12.0 | 6.0 | 6.0 |
| Dimethicon or Cyclomethicon fluid | 1.0 | 1.0 | 1.0 | 2.0 | 1.0 |
| Pplypropylene glycol 15 stearyl ether | 2.0 | 5.0 | 3.0 | — | 3.0 |
| Decyl glucoside/Stearic acid (Montanov 68 ™) | 5.0 | 5.0 | 8.0 | 6.0 | 6.0 |
| Polyethylene glycol 400 | 5.0 | 5.0 | 5.0 | — | — |
| Hexylene glycol | — | — | — | 8.0 | — |
| Water | — | — | — | — | 10.0 |
| Glycerin | To 100 | To 100 | To 100 | To 100 | To 100 |

All above formulations (A to E) demonstrated targeted effective beta carotene accumulation in hair follicles of pre-shaved skin mice after 1 or three hours of application.

Example 3

Sudan Black Pigment Cream

Three different formulations of a Sudan Black in oil-in-polyol vehicle were produced. Table 3 below lists the ingredients used in each of the formulations (A-C).

TABLE 3

| Ingredients | A % W/W | B % W/W | C % W/W |
|---|---|---|---|
| Sudan Black | 0.5 | 0.5 | 0.5 |
| Capric/Caprylic triglycerides | 6.0 | 6.0 | 6.0 |
| Isopropyl myristate | 6.0 | 6.0 | 6.0 |
| Glyceryl mono stearate | | 4.0 | 4.0 |
| Dimethicon or Cyclomethicon fluid | 1.0 | 1.0 | 1.0 |
| Pplypropylene glycol 15 stearyl ether | 2.0 | 2.0 | 0.0 |
| Decyl glucoside/Stearic acid (Montanov 68 ™) | 5.0 | 5.0 | 8.0 |
| Polyethylene glycol 400 | 5.0 | 5.0 | — |
| Water | — | — | 10.0 |
| Glycerin | To 100 | To 100 | To 100 |

All above formulations (A to C) demonstrated targeted effective Sudan Black accumulation in hair follicles.

Example 4

Steroid Formulation

Steroids were incorporated into oil-in-polyol emulsions with mean particle size below one micron. Table 4 below describes the ingredients used in formulating the Steroid containing oil-in-polyol emulsion.

TABLE 4

| Ingredients | A % W/W | B % W/W | C % W/W | D % W/W | E % W/W | F % W/W |
|---|---|---|---|---|---|---|
| Momethasone fuorate | 0.5 | | | 0.5 | | |
| Clobetasole | | 0.5 | | | 0.5 | |
| Dexamethasone | | | 0.5 | | | 0.5 |
| Capric/Caprylic triglycerides | 12.0 | 12.0 | 12.0 | 12.0 | 12.0 | 12.0 |
| Octyl dodecanol | 6.0 | 6.0 | 6.0 | 6.0 | 6.0 | 6.0 |
| Cetostearyl alcohol | 3.0 | 3.0 | 3.0 | 3.0 | 3.0 | 3.0 |
| Dimethicon or Cyclomethicon fluid | 1.0 | 1.0 | 1.0 | 1.0 | 1.0 | 1.0 |
| Polyoxyethylene (2) Stearyl Ether (Brij 71 ™) | 3.0 | 3.0 | 3.0 | 3.0 | 3.0 | 3.0 |
| Polyoxyethylene (21) Stearyl Ether (Brij 721 ™) | 2.0 | 2.0 | 2.0 | 2.0 | 2.0 | 2.0 |
| Water | — | — | — | 10.0 | 10.0 | 10.0 |
| Polyethylene glycol 400 | To 100 | To 100 | To 100 | To 100 | To 100 | To 100 |

All above formulations (A to C) demonstrated targeted effective Sudan Black accumulation in hair follicles.
The above steroids formulations A to F are of a mean droplet size of below one micron and are easy to apply, well absorbed and do not form film or skin debris and producing good skin feeling without greasiness or stickiness

Example 5

Anti-Biotic Emulsion

All above formulations (A to C) demonstrated targeted effective Sudan Black accumulation in hair follicles.
Two types of antibiotics were incorporated into an oil-in-polyol type sub-micron dro

TABLE 5

| Ingredients | Formulation A % W/W | B % W/W |
|---|---|---|
| Ciprofloxadin | 0.5 | |
| Doxycline | | 0.5 |
| Capric/Caprylic triglycerides | 12.0 | 12.0 |
| Octyl dodecanol | 6.0 | 6.0 |
| Cetostearyl alcohol | 3.0 | 3.0 |
| Dimethicon or Cyclomethicon fluid | 1.0 | 1.0 |
| Polyoxyethylene (2) Stearyl Ether (Brij 71 ™) | 3.0 | 3.0 |
| Polyoxyethylene (21) Stearyl Ether (Brij 721 ™) | 2.0 | 2.0 |
| Water | — | — |
| Polyethylene glycol 400 | To 100 | To 100 |

Drugs of formulation A and B were homogenously dissolved in the carrier or vehicle formulation of oil-in-polyol drug delivery formulation.

Example 6

Cyclosporin Emulsion

Cyclosporin was incorporated into oil-in-polyol type sub-micron droplet emulsion.

TABLE 6

| Ingredients | Formulation A % W/W | B % W/W |
|---|---|---|
| Cyclosporin | 0.5 | 0.5 |
| Capric/Caprylic triglycerides | 6.0 | 6.0 |
| Octyl dodecanol | 6.0 | 6.0 |
| Propylene Glycol Dicaprylocaprate (Labrafa ® PG) | 6.0 | — |
| Dimethyl isosorbide | 15.0 | 15.0 |
| Polyoxyethylene (2) Stearyl Ether (Brij 71 ™) | 3.0 | 3.0 |
| Polyoxyethylene (21) Stearyl Ether (Brij 721 ™) | 2.0 | 2.0 |
| Caprylocaproyl macrogolglycerides (labrasol ®) | — | 5.0 |
| Propylene glycol | 25.0 | 25.0 |
| Polyethylene glycol 400 | To 100 | To 100 |

Drugs of formulation A and B were homogenously dissolved in the carrier or vehicle formulation of oil-in-polyol drug delivery formulation.

Example 7

Itraconzole Emulsion

Itraconazole was incorporated oil-in-polyol type sub-micron droplet emulsion.

TABLE 7

| Ingredients | Formulation A % W/W | B % W/W |
|---|---|---|
| Itraconzole | 1.0 | 2.0 |
| Capric/Caprylic triglycerides | 10.0 | 10.0 |
| Propylene Glycol Monocaprylate (Capryol ™ 90) | 10.0 | 10.0 |
| Glyceryl monostearate | 4.0 | 4.0 |
| Sucrose stearate | 3.0 | 3.0 |
| Lauroyl Macrogolglycerides (Gelucire ® 44/14) | 8.0 | 8.0 |
| Citric acid | .05 | .05 |
| Propylene glycol | 15.0 | 15.0 |
| Polyethylene glycol 400 | To 100 | To 100 |

All above formulations (A to C) demonstrated targeted effective Sudan Black accumulation in hair follicles.
Drugs of formulation A and B were homogenously dissolved in the carrier or vehicle formulation of oil-in-polyol drug delivery formulation.

Example 8

Hair Strengthening Cosmetic Agent Emulsion

All above formulations (A to C) demonstrated targeted effective Sudan Black accumulation in hair follicles.
Herbal extract were incorporated into oil-in-polyol type sub-micron droplet emulsion. The Extracts were dissolved in the oils before homogenization.

TABLE 8

| Ingredients | Formula A % W/W | B % W/W | C % W/W |
|---|---|---|---|
| Rosemary extract | 2.0 | | |
| Saw Palmetto oil | | 2.0 | |
| Channelled Wrack extract | | | 2.0 |
| Capric/Caprylic triglycerides | 6.0 | 6.0 | 6.0 |
| Cetearyl octanoate | 3.0 | 3.0 | 3.0 |
| Glyceryl monostearate | 3.0 | 3.0 | 3.0 |
| Decyl glucoside/Stearic acid (Montanov 68 ™) | 5.0 | 5.0 | 5.0 |
| Polyethylene glycol 200 | 5.0 | 5.0 | 5.0 |
| Glycerin | To 100 | To 100 | To 100 |

Cosmetic agents of formulation A to C of this example were homogenously dissolved in the carrier or vehicle formulation of oil-in-polyol drug delivery formulation.

Example 9

Minoxidil Emulsion

Minoxidil was incorporated into oil-in-polyol type sub-micron droplet emulsion. Minoxidil was mixed with the oil phase and surfactants before homogenization at 70° C.

TABLE 9

| Ingredients | Formula A % W/W | B % W/W | C % W/W |
|---|---|---|---|
| Minoxidil | 1.0 | 2.0 | 5.0 |
| Capric/Caprylic triglycerides | 6.0 | 6.0 | 6.0 |
| Cetearyl octanoate | 3.0 | 3.0 | 3.0 |
| Glyceryl monostearate | 3.0 | 3.0 | 3.0 |
| Decyl glucoside/Stearic acid (Montanov 68 ™) | 6.0 | 6.0 | 6.0 |
| Dimethil isosorbide | 15.0 | — | 15.0 |
| Diethylene Glycol Monoethyl Ether (Transcutol ® HP) | — | 25.0 | 25.0 |
| Polyethylene glycol 200 | 5.0 | 5.0 | 5.0 |
| Glycerin | To 100 | To 100 | To 100 |

Example 10

Keratinocyte Growth Factor Emulsion

Keratinocyte growth factor was incorporated extemporaneously in ready vehicle of oil-in-polyol type sub-micron droplet emulsion.

TABLE 10

| Ingredients | Formula A % W/W |
|---|---|
| Keratinocyte growth factor | 0.05 |
| Capric/Caprylic triglycerides | 10.0 |
| Decyl glucoside/Stearic acid (Montanov 68 ™) | 6.0 |
| Polyethylene glycol 200 | 15.0 |
| Glycerin | To 100 |

Example 11

Hair Removal Emulsion

Colorizing agents, for example, black or a dark coloring agent may be incorporated within the emulsion to enhance lazer light hair removal, as is known to the skilled artisan. One embodiment of such an emulsion is as set forth in Table 11 below.

TABLE 11

| Ingredients | Formula A % W/W | B % W/W | C % W/W | D % W/W |
|---|---|---|---|---|
| Cosmetic colorants: Green 6/Red 18/Violet 2 or Green 6/Red 17 (FDC #) | 0.5 | 0.5 | 0.5 | 0.5 |
| Capric/Caprylic triglycerides | 8.0 | 8.0 | 8.0 | 8.0 |
| Propylene glycol monocaprylate | 8.0 | 8.0 | 8.0 | 8.0 |
| Sucrose ester (Sisterna ™ 50) | — | — | 3.0 | 3.0 |
| Decyl glucoside/Stearic acid (Montanov 68 ™) | 6.0 | 4.0 | — | — |
| Sepigel 305 ™ | — | 0.3 | — | 0.3 |
| Water purified | 5.0 | 5.0 | 5.0 | 5.0 |
| Polyethylene glycol 400 | 5.0 | 5.0 | 5.0 | 5.0 |
| Glycerin | To 100 | To 100 | To 100 | To 100 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of targeting a bio-active agent in hair follicles, comprising:
   topically applying to skin and hair follicles until well absorbed a cream composition of oil-in-polyol emulsion having a mean particle size of 200 to 2000 nanometers, containing (a) a dissolved bio-active agent selected from the group consisting of a depilatory, a coloring agent that facilitates laser photothermolysis, a coloring agent applied for cosmetic hair coloring, an anti-inflammatory agent, a hair growing agent, an antibiotic for *propionibacterium acne*, a retinoid, an anti-fungal agent, and an immune-modulator, (b) an oil, (c) from about 60 to about 90% by weight of a polyol, and (d) a stabilizer;
   wherein said bio-active agent is dissolved in the oil base of said emulsion, and accumulated within hair follicles.

2. The method of claim 1, wherein the bio-active agent is a depilatory.

3. The method of claim 1, wherein the bio-active agent is a coloring agent that facilitates laser photothermolysis.

4. The method of claim 1, wherein the bio-active agent is a hair growing agent.

5. The method of claim 1, wherein said composition further comprises an anti-inflammatory agent.

6. The method of claim 1, wherein the bio-active agent is a coloring agent applied for cosmetic coloring of hair.

7. The method of claim 1, wherein the mean particle size is 200 to 1,000 nanometers.

8. The method of claim 1, wherein the mean particle size is 300 to 800 nanometers.

9. The method of claim 1, wherein the bio-active agent is an antibiotic for *propionibacterium acne*.

10. The method of claim 1, wherein the bio-active agent is vitamin A.

11. The method of claim 1, wherein the bio-active agent is an anti-fungal.

12. The method of claim 1, wherein the bio-active agent is an immune-modulator.

* * * * *